United States Patent [19]

Kolich et al.

[11] Patent Number: 5,190,905

[45] Date of Patent: Mar. 2, 1993

[54] ASYMMETRIC HYDROGENATION OF AROMATIC-SUBSTITUTED OLEFINS USING METAL OR METAL ALLOY CATALYSTS

[75] Inventors: Charles H. Kolich; Thanikavelu Manimaran; W. Dirk Klobucar, all of Baton Rouge, La.

[73] Assignee: Ethyl Corporation, Richmond, Va.

[21] Appl. No.: 716,014

[22] Filed: Jun. 17, 1991

[51] Int. Cl.$^5$ .................. B01J 31/00; C07F 00/00; C07F 15/00; C07C 63/04

[52] U.S. Cl. .................. 502/162; 556/136; 556/146; 556/21; 562/493; 562/496

[58] Field of Search .................. 562/493, 496; 556/21, 556/136, 146; 502/162

[56] References Cited

U.S. PATENT DOCUMENTS

| | | | |
|---|---|---|---|
| 3,748,332 | 7/1973 | Wilkinson | 260/270 R |
| 3,793,355 | 2/1974 | Wilkinson | 260/429 R |
| 3,878,122 | 4/1975 | Pennella | 252/411 R |
| 4,268,454 | 5/1981 | Pez et al. | 260/439 R |
| 4,440,936 | 4/1922 | Riley | 562/496 |
| 4,506,030 | 3/1985 | Jones | 502/155 |
| 4,604,474 | 8/1986 | Kumobayashi et al. | 556/7 |
| 4,605,750 | 8/1986 | Kumobayashi et al. | 556/7 |
| 4,691,037 | 9/1987 | Yoshikawa et al. | 556/18 |

OTHER PUBLICATIONS

Alcock et al. Tetrahedron Asymmetry vol. 2, No. 1, p. 47 (1991).

Primary Examiner—Paul J. Killos
Assistant Examiner—Joseph M. Conrad
Attorney, Agent, or Firm—Richard J. Hammond

[57] ABSTRACT

A process for the asymmetric reduction of carboxylic acids of the formula

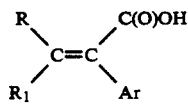

or the amine salts thereof, where R and $R_1$ are the same or different and are hydrogen, alkyl, cycloalkyl or haloalkyl and Ar is aryl or substituted aryl is disclosed.

17 Claims, No Drawings

ASYMMETRIC HYDROGENATION OF AROMATIC-SUBSTITUTED OLEFINS USING METAL OR METAL ALLOY CATALYSTS

FIELD OF THE INVENTION

This invention relates to a process for the catalytic reduction of aromatic-substituted olefins. More specifically, this invention relates to a process for asymmetrically, catalytically reducing aromatic-substituted olefins using a mixture of a solid metal or metal alloy that has been treated with an optically active organophosphorous compound.

BACKGROUND OF THE INVENTION

Enantioselective catalysis using chiral metal complexes provides one of the most general and flexible methods for achieving asymmetric organic reactions. Metallic elements possess a variety of catalytic activities, and permutations of organic ligands or other auxiliary groups directing the steric course of the reaction are practically unlimited. Efficient ligands must be endowed with, for example, suitable functionality, appropriate chirality, a structure capable of differentiating space either electronically or sterically and skeletal rigidity or flexibility.

Among the asymmetric organic reactions catalyzed by chiral transition metal complexes, asymmetric hydrogenation has been one of the best studied, due in large part to the fact that it is the basis for the first commercialized catalytic asymmetric process. See, for example, ApSimon, et al., *Tetrahedron*, 1986, 42, 5157.

Some of the more interesting of the asymmetric hydrogenation catalysts are those derived from BINAP [2,2'-bis(diphenylphosphino)-1,1'-binaphthyl]. See, for example, U.S. Pat. Nos.: 4,691,037; 4,739,084; 4,739,085; 4,764,629; 4,994,607; and 4,766,227. Unlike the more classical models of chiral (asymmetric) molecules, chirality in the case of the BINAP-type compounds arises from the restricted rotation about the single bond joining the naphthalene rings. Isomers arising from this type of asymmetry are termed atropisomers.

BINAP-based Ru(II) and Rh(I) complexes induce high enantioselectivity in catalytic reactions. See Noyori and Takaya, *Acc. Chem. Res.*, 1990, 23, 345.

The BINAP ruthenium complexes are dramatioally different than the rhodium ones. They have been used to catalyze a variety of asymmetric hydrogenations, including the hydrogenation of enamides and alkyl and aryl-substituted acrylic acids. See Noyori, et al., *Modern Synthetic Methods*, 1989, 5, 115, incorporated herein by reference. Unlike the rhodium catalyzed reductions, ruthenium(II) carboxylate complexes possessing the BINAP ligand are efficient catalysts for the enantioselective hydrogenation of $\alpha,\beta$-unsaturated carboxylic acids. According to Ohta, et al, *J. Org. Chem*, 52, 3174 (1982), the carboxyl moiety of the substrate, and not other oxygen containing groups, is responsible for the stereoselective reaction. Asymmetric reductions of non-carboxyl-containing substrates by ruthenium complexes are inefficient.

The preparation of the BINAP-bearing ruthenium complexes, while not only sophisticated, is time consuming and expensive. Another disadvantage of using the BINAP ruthenium complexes for the asymmetric hydrogenation of olefins is the high solubility of the complexes in solvents used for hydrogenation. This characteristic increases the complexity of product purification and makes recycle of the expensive catalyst difficult if not impossible. Accordingly, it would be advantageous to be able to carry out these enantioselective transformations using an insoluble heterogeneous catalyst that could be easily separated for recycle (by filtration, for example) from the hydrogenation reaction mixtures, while at the same time providing a reaction product free of catalyst contamination. However, a generally recognized disadvantage of heterogeneous catalysis relative to homogeneous catalysis is a decreased selectivity. See, for example, H. Brunner in "Topics in Stereochemistry", Vol. 18, p. 134, Ed. by E. L. Eliel and S. H. Wilen, John Wiley & Sons, New York (1988).

SUMMARY OF THE INVENTION

The present invention involves a novel method for the use of solid metals or metal alloys which, after treatment with compounds having optical activity, can be used as efficient catalysts to effect the asymmetric reduction of certain unsaturated organic compounds.

DESCRIPTION OF THE PREFERRED EMBODIMENTS

In the present specification, alkyl means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl, and eicosyl.

Cycloalkyl means cyclic alkyl having 3 to 7 carbon atoms and includes cyclopropyl, cyclobutyl, cyclopentyl, cyclohexyl and cycloheptyl.

Substituted aryl means phenyl or naphthyl substituted by at least one substituent selected from the group consisting of halogen (chlorine, bromine, fluorine or iodine), amino, nitro, hydroxy, alkyl, alkoxy, which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, haloalkyl which means straight or alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl and 2,2,3,3-tetrafluoropropyl.

Haloalkyl means straight or branched chain alkyl having 1 to 10 carbon atoms which is substituted by at least one halogen as mentioned above.

Phenylalkyl means that the alkyl moiety is straight or branched chain alkyl having 1 to 8 carbon atoms and includes, for example, benzyl, 2-phenylethyl, 1-phenylethyl, 3-phenylpropyl, 4-phenylbutyl, 5-phenylpentyl, 6-phenylhexyl and 8-phenyloctyl.

Substituted phenylalkyl means above-mentioned phenylalkyl which is substituted by at least one substituent selected from the group consisting of halogen, amino, nitro, hydroxy, alkyl, alkoxy and haloalkyl on the phenyl nucleus.

Chiral phosphine compound means an optically active alkyl or aryl substituted trivalent phosphorous compound. Examples of such compounds are:

1,2-ethanediyl-bis(o-methoxyphenyl)phenylphosphine (DIPAMP);

N,N'-bis(α-methylbenzyl)-N,N'-bis(diphenylphosphine) ethylenediamine (PNNP);

2,3-bis(diphenylphosphino)butane (CHIRAPHOS);

1,2-bis(diphenylphosphino)propane (PROPHOS);

2,3-O-isopropylidene-2,3-dihydroxy-1,4-bis(diphenylphosphino)butane (DIOP);

2,4-t-butyl 4-(diphenylphosphino)-2-(diphenylphosphino-methyl)-1-pyrrolidine-carboxylate (BPPM);

2,4-bis(diphenylphosphino)pentane (SKEWPHOS);

2,5-bis(diphenylphosphino)hexane (BDPH);

1,2-bis(diphenylphosphino)-1-phenylethane (PHENPHOS);

1,2-bis(diphenylphosphino)-1-cyclohexylethane (CYCPHOS);

α-[1,2-bis(diphenylphosphino)ferrocenyl]-ethyldimethylamine (BPPFA); and trans-4,5-bis[(5H-dibenzophospholyl)methyl]-2,2-dimethyl-1,3-dioxolane (DIPHOL).

A detailed description of suitable phosphines for the present invention is disclosed in "*Asymmetric Synthesis*", Vol. 5, Ed. by James D. Morrison, Academic Press, Orlando (1985), incorporated herein by reference.

The enantioselective preparations of the present invention are carried out optionally using amine salts of α-aryl olefinic carboxylic acids. When amine salts are used, they are derived from a wide variety of primary, secondary or tertiary hydrocarbyl amines. They include the aromatic amines, aliphatic amines, mixed aromatic/aliphatic amines, as well as heterocyclic and cycloaliphatic amines. Such hydrocarbyl amino compounds are illustrated by methylbenzylamine, ethyldiisopropylamine, N-methylpiperidine, triethylamine, pyrrole, etc. They react readily with the carboxylic acid function of the α-aryl olefinic carboxylic acid to produce amine salts, usually by preparing a solution of equimolar amounts of the two reactants. The resulting amine salts, generated in situ or preformed, are used in the subsequent step of the process of this invention.

The carboxylic acids have the formula

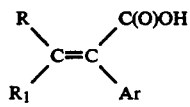

where R and $R_1$ are the same or different and are hydrogen, alkyl, cycloalkyl, or haloalkyl and Ar is aryl or substituted aryl. Preferably R and R are the same or different and are hydrogen or alkyl. The amine salts are also useful in the process of the present invention. Most preferred in the above carboxylic acid is where R and $R_1$ are the same and are hydrogen or methyl. They are reduced (hydrogenated) asymmetrically by a catalytic process employing a mixture of (i) a metal or metal alloy and (ii) an optically active organophosphorous compound in an appropriate solvent where the compound is

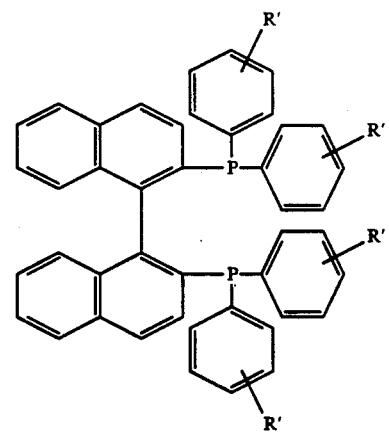

where R' is hydrogen (BINAP), alkyl, haloalkyl, aryl or substituted aryl. It is neither necessary nor economically desirable to isolate the chiral metal catalyst that may be formed in this mixture prior to hydrogenation of the substrate.

The metal or metal alloy of use in this invention may be any of a wide variety of forms and include, for example, ruthenium metal, either as its alloy or in pure form, nickel metal either as its alloys (stainless steels) or in treated form (Raney nickel or supported nickel), chromium-nickel alloys, iron-nickel alloys, molybdenum-nickel alloys, or iron chromium alloys.

Preferably, the metals of use in the process of the present invention include the stainless steels (e.g., 316 SS, 304 SS, 410 SS), nickel chromium alloy (45% Ni, 55% Cr) and molybdenum nickel alloy (87% Ni, 12.5% Mo). The form of the metals of use herein is typically as a finely divided powder having a particle size that is smaller than 25 mesh (Standard Sieve).

The chiral organophosphorous compound admixed with the metal or metal alloy is preferably one where all R' are the same and are hydrogen or $C_1$ to $C_6$ linear or branched alkyl. Most preferably all R' are the same and are hydrogen, methyl, ethyl, propyl or isopropyl.

Activation of the metal for asymmetric hydrogenation is achieved by combining (i) and (ii) in an appropriate solvent at 50° C. to 150° C. under a hydrogen pressure of 5 to 300 atmospheres for a time of one to five hours or more. While it is possible (and convenient) to use the same solvent for both metal activation and hydrogenation, a change of solvent may be desirable. For instance, toluene is a preferred solvent for the metal activation step due to its ability to dissolve (ii), while methanol is a preferred solvent for hydrogenation due to its ability to dissolve hydrogen.

The asymmetric catalytic hydrogenations utilizing the catalyst mixture of (i) and (ii) above is mixed with a solution of an α-aryl olefinic carboxylic acid or its amine salt, typically in a ratio of (i):(ii) of 10:1 to 1:10, preferably 8:1 to 1:8, most preferably 3:1 on a weight basis.

The weight ratio of (i) to the olefinic acid or its amine salt is between about 1 to 20 to about 1 to 20,000, preferably about 1 to 100 to about 1 to 10,000, most preferably about 1 to 5,000 to about 1 to 10,000.

The combination of the catalyst mixture, the olefinic carboxylic acid (or amine salt of such acid) and suitable organic solvent, provide a system suitable for hydrogenation at elevated hydrogen pressure, i.e., pressures above about 75 psig.

Unlike the known homogeneous asymmetric hydrogenation catalysts which give colored reaction solutions due to the dissolved metal complex, heterogeneous systems of the present invention give clear colorless solutions after a simple filtration to remove the solid metal catalyst. The catalyst can be recycled directly or reactivated by another treatment with the optically active organophosphorous compound as described above. The colorless reaction filtrate contains the saturated asymmetric carboxylic acid free of any metal contamination.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

GENERAL

All solvents used in the hydrogenation were reagent grade and were sparged with nitrogen for at least 2 hours to remove oxygen. The S-BINAP, alloys and the metals used are commercially available materials. Conversions were determined by GC (area %). Optical purities were determined by HPLC using a chiral column. The hydrogenation reactors were constructed of Monel 400 or T316 Stainless Steel.

EXAMPLE 1

A 62 mg (0.10 mmol) portion of (S)-(−)bis(diphenylphosphino)-1,1′-binaphthyl (S-BINAP), 171 mg of 316-L stainless steel powder (325 mesh), and 30 ml of methanol were combined in a 100-ml 316 stainless steel pressure reactor. The reactor was flushed with hydrogen (3×300 psi) and stirred at 300 rpm with 1000 psi $H_2$ for 1 hour at 60° C. and then 3 hours at 100° C. The reactor was cooled to room temperature and vented. A solution of 288 mg (1.41 mmol) of 2-(4-isobutylphenyl)acrylic acid (UA) in 10 ml of methanol was added to the vessel in a nitrogen-filled glove box. The reactor was flushed (3×300 psi $H_2$): and stirred (300 rpm) with 1000 psi $H_2$: at 60° C. After a total of 72 hours, the conversion of UA to ibuprofen was 31%, and the optical purity of the product was 91% (S) by HPLC.

EXAMPLE 2

Example 1 was repeated using toluene in place of methanol for the treatment of the stainless steel powder with S-BINAP. A 67 mg (0.11 mmol) portion of S-BINAP dissolved in 30 ml of toluene was combined with 306 mg of 316-L stainless steel powder (325 mesh) in a 100-ml 316 stainless steel pressure reactor. The reactor was flushed (3×300 psi $H_2$): and stirred (700 rpm) with 1000 psi $H_2$: for 3 hours at 100° C. The reactor was then cooled to 40° C. and vented. The toluene was completely removed from the reactor by vacuum distillation. A solution of 298 mg (1.46 mmol) of UA in 40 ml of methanol was added to the reactor in a nitrogen-filled glove box. The reactor was flushed (3×300 psi $H_2$) and stirred at 700 rpm/1000 psi $H_2$/22° C. After 2 hours, a GC of the clear colorless reaction solution indicated the UA was unchanged. The reaction temperature was increased to 60° C. and after 2.5 hours (1000 psi $H_2$/700 rpm) the conversion of UA to ibuprofen was 42%. After 5 hours at 60° C./1000 psi $H_2$/700 rpm, the hydrogenation was complete and the optical purity of the product was 74% (S) by HPLC.

EXAMPLE 3

The clear colorless reaction solution from Example 2 was decanted from the solid catalyst in the reactor in a nitrogen-filled glove box. The reactor was then charged with a solution of 309 mg (1.51 mmol) of UA in 40 ml of methanol. The reactor was flushed (3×300 psi $H_2$) and stirred (700 rpm) with 1000 psi $H_2$ at 21° C. After 2 hours, a GC analysis for the clear colorless reaction solution showed the UA was unchanged so the reaction was continued at 60° C./1000 psi $H_2$/700 rpm. After 21 hours, the conversion of UA to ibuprofen was 53% and the optical purity was 80% (S). After 43 hours, the conversion reached 80% with a product optical purity of 77% (S).

EXAMPLE 4

A 66 mg (0.106 mmol) portion of S-BINAP, 575 mg of 410-L stainless steel powder (325 mesh) and 30 ml of methanol were combined in a 100-ml Monel pressure reactor. The reactor was flushed with hydrogen (3×300 psi) and stirred (300 rpm) with 1000 psi hydrogen for 3 hours at 100° C. The vessel was cooled to room temperature and allowed to stir at room temperature for 67 hours. The reactor was vented and a solution of 397 mg (1.95 mmol) of UA in 10 ml of methanol was added to the vessel in a nitrogen-filled glove box. The reactor was flushed with hydrogen (3×300 psi) and stirred with 1000 psi hydrogen at 60° C. for 24 hours. GC showed the conversion to ibuprofen was 16%. The reaction was continued for 24 hours at 100° C. with 1000 psi hydrogen. The conversion of UA to ibuprofen was 56% and the optical purity was 67% (S).

EXAMPLE 5

Example 4 was repeated using 630 mg of 304-L stainless steel powder, 50 mg (0.08 mmol) S-BINAP and 357 mg (1.75 mmol) UA. The conversion to ibuprofen was 17% and the optical purity was 91% (S).

EXAMPLE 6

A 67 mg (0.108 mmol) portion of S-BINAP, 552 mg of Ni-Fe alloy (100 mesh, 80:20) and 40 ml of methanol were combined in a 100-ml Monel pressure reactor in a nitrogen-filled glove box. The reactor was flushed with hydrogen (3×300 psi) and stirred at 100° C. with 1000 psi hydrogen for 3 hours. The reactor was cooled to room temperature and vented. A solution of 406 mg (1.99 mmol) of UA in 10 ml of methanol was added to the reactor in a nitrogen-filled glove box. The reactor was flushed with hydrogen and stirred with 1000 psi hydrogen at 60° C. for 20 hours. GC showed no conversion to ibuprofen. The reaction mixture was stirred 24 hours at 100° C. with 1000 psi hydrogen. The conversion of UA to ibuprofen was 4% and the optical purity was 97% (S).

EXAMPLE 7

To a 100-ml Monel pressure reactor in a glove box (nitrogen purged) was added 568 mg of Ni-Mo alloy (325 mesh, 87.5:12.5), 65 mg (0.105 mmol) S-BINAP and 50 ml of methanol. The reactor was flushed with hydrogen (3×300 psi) and stirred (600 rpm) for 3 hours with 1000 psi hydrogen at 100° C. The reactor was cooled and vented. A solution of 301 mg (1.48 mmol) of UA in 10 ml of methanol was added to the reactor in a nitrogen-filled glove box. The reactor was flushed with hydrogen (3×300 psi) and stirred (600 rpm.) at 60° C. for 17 hours with 1000 psi hydrogen. GC showed 0% conversion to ibuprofen. The reaction mixture was stirred (600 rpm) for 21 hours at 100° C. with 1000 psi hydrogen. The conversion of UA to ibuprofen was 22% and the optical purity was 70% (S).

EXAMPLE 8

To a 100-ml Monel pressure reactor in a nitrogen-filled glove box was added 566 mg of Cr-Ni alloy (60 mesh, 55:45), 56 mg (0.090 mmol) S-BINAP and 50 ml of methanol. The reactor was flushed with hydrogen and stirred (600 rpm) at 100° C. with 1000 psi hydrogen for 3 hours. The reactor was cooled and vented. A solution of 302 mg (1.48 mmol) of UA in 10 ml of methanol was added to the reactor in a nitrogen-filled glove box. The reactor was sealed, flushed with hydrogen and warmed to 60° C. The reactor was stirred (600 rpm) at 60° C. for 17 hours with 1000 psi hydrogen. GC showed 0% conversion to ibuprofen. After purging with hydrogen, the reactor was stirred (600 rpm) for 21 hours at 100° C. with 1000 psi hydrogen. GC showed 22% conversion of UA to ibuprofen of 70% (S) optical purity.

EXAMPLE 9

To a 100 ml Monel pressure reactor was added 72 mg of wet Raney Nickel® catalyst, 99 mg (0.159 mmol) S-BINAP and 30 ml of methanol. The reactor was sealed, purged with hydrogen and stirred (300 rpm) of 3 hours at 60° C. then 3 hours at 100° C. with 1000 psi hydrogen. The reactor was cooled and vented. In a nitrogen-filled glove box, a solution of 508 mg (2.49 mmol) of UA in a 10 ml of methanol was added to the reactor. The vessel was sealed, purged with hydrogen and stirred for 17 hours at 23° C. with 1000 psi. GC analysis of the reaction mixture showed 10% conversion of UA to ibuprofen of 90% (S) optical purity. The reaction mixture was stirred for 54 hours at 60° C. and sampled periodically for conversion and optical purity (see Table). As conversion increased, the enantioselectivity decreased until a nearly racemic product (4% ee) was obtained at 94% conversion (54 hours/60° C).

EXAMPLE 10

Example 9 was repeated using 10 mg of Harshaw Ni-P5124 (60% Ni on $Al_2O_3/SiO_2$), 79 mg (0.127 mmol) S-BINAP and 30 ml of methanol. The reactor was sealed, purged with hydrogen and stirred (300 rpm) for 3 hours at 60° C. and 3 hours at 100° C. with 1000 psi hydrogen. The reactor was cooled and vented. A solution of 518 mg (2.54 mmol) of UA in 10 ml of methanol was added to the reactor in a nitrogen-filled glove box. The reactor was sealed, flushed with hydrogen and stirred at 23° C. for 17 hours with 1000 psi hydrogen. GC analysis of the reaction mixture showed 4% conversion of UA to ibuprofen of 100% (S) optical purity. The mixture was stirred with 1000 psi $H_2$ for 24 hours at 60° C. with no change in the conversion followed by 24 hours at 100° C. The conversion of UA to ibuprofen was 11% and the optical purity was 90% (S).

EXAMPLE 11

Example 2 was repeated using 336 mg of ruthenium powder (325 mesh) in place of the 316-L stainless steel powder and 66 mg (0.11 mmol) of S-BINAP. After completing the catalyst preparation and removing the toluene under vacuum, a 329 mg (1.61 mmol) portion of UA in 40 ml of methanol was added to the reactor in a nitrogen-filled glove box. The reactor was flushed (3×300 psi $H_2$) and then stirred (700 rpm) at 25° C. with 1000 psi hydrogen. After 4 hours, a GC analysis of the clear colorless reaction solution showed a 51% conversion of UA to ibuprofen (34% ee by HPLC). After 7 hours, the conversion was 60% (24% ee), and after 23 hours, the conversion reached 91% (16% ee).

TABLE

HETEROGENEOUS ASYMMETRIC HYDROGENATION RESULTS WITH S-BINAP TREATED METALS AND ALLOYS (900-1000 psi $H_2$ IN METHANOL)

| EXAMPLE | SUBSTRATE/REACTOR CONSTRUCTION* | METAL OR METAL ALLOY | METAL/S-BINAP TREATMENT | |
|---|---|---|---|---|
| | | | SOLVENT | TEMP/TIME/PRESS. (°C./hr/psi) |
| 1 | UA/SS | 316-L SS powder[a] 325 mesh | Methanol | 60/1/1000 100/3/1000 |
| 2 | UA/SS | 316-L SS powder[a] 325 mesh | Toluene | 100/3/1000 |
| 3 | UA/SS | 316-L SS powder[a] 325 mesh (Recycled catalyst from Example 2) | — | — |
| 4 | UA/M | 410-L SS powder[b] 325 mesh | Methanol | 100/3/1000 |
| 5 | UA/M | 304-L SS powder[c] 100 mesh | Methanol | 100/3/1000 |
| 6 | UA/M | Ni—Fe alloy (80:20) 100 mesh | Methanol | 100/3/1000 |
| 7 | UA/M | Ni—Mo alloy | Methanol | 100/3/1000 |

TABLE-continued
HETEROGENEOUS ASYMMETRIC HYDROGENATION RESULTS WITH S-BINAP TREATED METALS AND ALLOYS (900-1000 psi H₂ IN METHANOL)

| | | | | |
|---|---|---|---|---|
| 8 | UA/M | (87.5:12.5) 325 mesh Ni—Cr Alloy (45:55) 60 mesh | Methanol | 100/3/1000 |
| 9 | UA/M | Raney Ni | Methanol | 60/3/1000 |
| | | | | 100/3/1000 |
| 10 | UA/M | Ni/SiO$_2$Al$_2$O$_3$$^d$ | Methanol | 60/3/1000 |
| | | | | 100/3/1000 |
| 11 | UA/SS | Ru powder 325 mesh | Methanol | 100/3/1000 |

| EXAMPLE | HYDROGENATION RUN TEMP (°C.)/TIME (hr) | CONVERSION (GC AREA %) | % ee |
|---|---|---|---|
| 1 | 60/7.5 | 13 | 97(S) |
| | 60/72 | 31 | 91(S) |
| 2 | 22/2 | 0 | |
| | 60/2.5 | 42 | |
| | 60/5 | 100 | 74(S) |
| 3 | 60/21 | 53 | 80(S) |
| | 60/43 | 80 | 77(S) |
| 4 | 60/24 | 16 | |
| | 100/24 | 56 | 67(S) |
| 5 | 60/24 | 7 | |
| | 100/24 | 17 | 91(S) |
| 6 | 60/20 | 0 | |
| | 100/24 | 4 | 97(S) |
| 7 | 60/17 | 0 | |
| | 100/21 | 22 | 70(S) |
| 8 | 60/17 | 0 | |
| | 100/21 | 61 | 29(S) |
| 9 | 23/17 | 10 | 90(S) |
| | 60/5 | 21 | 72(S) |
| | 60/24 | 63 | 30(S) |
| | 60/54 | 94 | 4(S) |
| 10 | 23/17 | 4 | 100(S) |
| | 60/24 | 4 | |
| | 100/24 | 11 | 90(S) |
| 11 | 25/4 | 51 | 34(S) |
| | 25/7 | 60 | |
| | 25/23 | 91 | |

*Reactor construction: M = Monel; SS = 316 Stainless Steel.
$^a$68% Fe, 17% Cr, 13% Ni and 2% Mo.
$^b$87.5% Fe and 12.5% Cr.
$^c$70% Fe, 19% Cr and 11% Ni.
$^d$Harshaw 5124, 60% Ni on silica/alumina.
ee = enantiomeric excess (optical purity).

We claim:

1. A process for preparing optically active α-aryl aliphatic carboxylic acids which comprises catalytically, asymmetrically hydrogenating a carboxylic acid of the formula

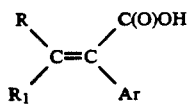

or the amine salt thereof, where R and R$_1$ are the same or different and are hydrogen, alkyl, cycloalkyl, or haloalkyl; and Ar is aryl or substituted aryl; by utilizing a catalytically effective amount of a mixture of (i) metal or metal alloy activated with hydrogen and (ii) a chiral phosphine compound.

2. The process according to claim 1 wherein said metal or metal alloy is ruthenium, ruthenium alloy, nickel, nickel alloy or iron chromium alloy.

3. The process according to claim 1 wherein said metal alloy is 316 SS alloy.

4. The process of claim 1 wherein R and R$_1$ are the same or different and are hydrogen or alkyl.

5. The process according to claim 4 wherein R and R$_1$ are hydrogen.

6. The process according to claim 1 wherein Ar is phenyl or naphtyhl substituted with alkyl or alkoxy.

7. The process according to claim 6 wherein Ar is phenyl substituted with methyl, ethyl, n-propyl or isobutyl.

8. A process for preparing S-ibuprofen which comprises catalytically, asymmetricaly hydrogenating 2-(4-isobutylphenyl)acrylic acid or its amine salt by utilizing a mixture of ruthenium, a ruthenium alloy, nickel, a nickel alloy or an iron-chromium alloy and S-BINAP where BINAP is

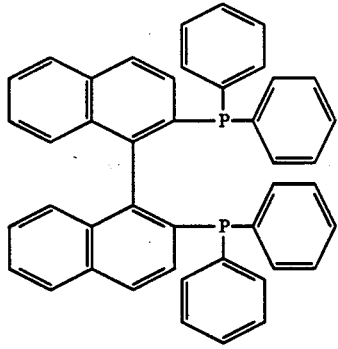

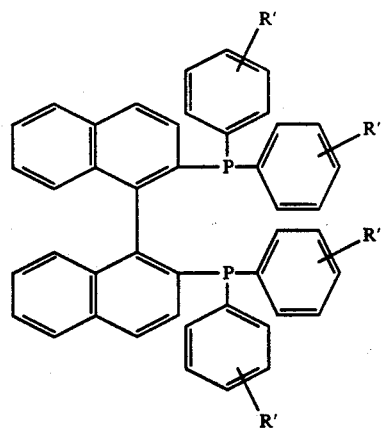

9. A process for preparing optically active α-aryl aliphatic carboxylic acids which comprises catalytically, asymmetrically hydrogenating a carboxylic acid of the formula

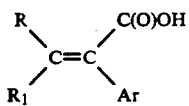

or the amine salt thereof, where R and $R_1$ are the same or different and are hydrogen, alkyl, cycloalkyl, or haloalkyl; and Ar is aryl or substituted aryl; by utilizing a mixture of (i) a metal or metal alloy activated with hydrogen and (ii) an optically active ligand where the ligand is where R' is hydrogen (BINAP), alkyl, haloalkyl, aryl or substituted aryl.

10. The process according to claim 9 wherein said metal is nickel, nickel alloy or iron-chromium alloy.

11. The process according to claim 10 wherein said metal alloy is 316 SS alloy.

12. The process of claim 9 wherein R and R' are the same or different and are hydrogen or alkyl.

13. The process according to claim 12 wherein R and $R_1$ are hydrogen.

14. The process according to claim 9 wherein Ar is phenyl or naphthyl substituted with alkyl or alkoxy.

15. The process according to claim 14 wherein Ar is phenyl substituted with methyl, ethyl, n-propyl or iso-butyl.

16. An asymmetric hydrogenation catalyst composition comprising a mixture of (i) a chiral phosphine and (ii) a metal or metal alloy activated with hydrogen and optionally an organic amine and hydrogen.

17. The composition according to claim 16 wherein the chiral phosphine compound is BINAP and the metal is 316 stainless steel.

* * * * *